(12) United States Patent
Corbett et al.

(10) Patent No.: US 10,406,527 B2
(45) Date of Patent: Sep. 10, 2019

(54) THERMOCYCLER

(71) Applicant: Bio Molecular Systems Pty Ltd, Upper Coomera (AU)

(72) Inventors: John Corbett, Sovereign Island (AU); Jason Austin, Upper Coomera (AU)

(73) Assignee: BIO MOLECULAR SYSTEMS PTY LTD, Upper Coomera, Queensland (AU)

(*) Notice: Subject to any disclaimer, the term of this patent is extended or adjusted under 35 U.S.C. 154(b) by 221 days.

(21) Appl. No.: 15/029,345

(22) PCT Filed: Oct. 15, 2014

(86) PCT No.: PCT/AU2014/000983
§ 371 (c)(1),
(2) Date: Apr. 14, 2016

(87) PCT Pub. No.: WO2015/054733
PCT Pub. Date: Apr. 23, 2015

(65) Prior Publication Data
US 2016/0263579 A1  Sep. 15, 2016

(30) Foreign Application Priority Data

Oct. 15, 2013  (AU) ................................ 2013903960

(51) Int. Cl.
*B01L 3/00* (2006.01)
*B01L 1/00* (2006.01)
(Continued)

(52) U.S. Cl.
CPC .............. *B01L 7/52* (2013.01); *C12Q 1/6846* (2013.01); *G01N 35/00584* (2013.01);
(Continued)

(58) Field of Classification Search
CPC .............. B01L 7/52; B01L 2300/0803; B01L 3/50851; B01L 2300/1816; B01L 3/502715; B01L 2200/147; B01L 2300/1811
See application file for complete search history.

(56) References Cited

U.S. PATENT DOCUMENTS

2002/0047003 A1  8/2002  Bedingham et al.
2002/0113066 A1  8/2002  Stark et al.
(Continued)

FOREIGN PATENT DOCUMENTS

EP  1 010 979  6/2000
EP  1 649 931  4/2006
(Continued)

OTHER PUBLICATIONS

Written Opinion dated Feb. 20, 2017 in corresponding Singapore Application No. 11201602758Y.
(Continued)

*Primary Examiner* — Nathan A Bowers
(74) *Attorney, Agent, or Firm* — Wenderoth, Lind & Ponack, L.L.P.

(57) ABSTRACT

The present invention provides a thermocycler comprising: a rotatable platform having a plurality of reaction wells or being adapted to receive a plurality of reaction containers, wherein the rotatable platform and/or the reaction wells are formed, at least in part, of a material which is adapted to be inductively heated by exposure to electromagnetic energy. An electromagnetic energy source is provided and is configured to direct electromagnetic energy at the rotatable platform, wherein the electromagnetic energy source surrounds a sufficient amount of the rotatable platform in order to heat the entire platform substantially simultaneously. In preferred embodiments, the electromagnetic energy source completely surrounds the rotatable platform. The invention
(Continued)

further comprises a method of cycling a reaction mixture between predetermined temperatures utilising the novel thermocycler apparatus of the invention. The invention also comprises use of the novel thermocycler apparatus of the invention for conducting a nucleic acid amplification reaction such as the polymerase chain reaction (PCR) and the ligase chain reaction (LCR).

17 Claims, 4 Drawing Sheets

(51) Int. Cl.
| | |
|---|---|
| B01L 7/00 | (2006.01) |
| H05B 6/10 | (2006.01) |
| C12Q 1/6844 | (2018.01) |
| G01N 35/00 | (2006.01) |
| G01N 35/02 | (2006.01) |
| G01N 35/04 | (2006.01) |
| B01L 9/06 | (2006.01) |

(52) U.S. Cl.
CPC .......... *G01N 35/025* (2013.01); *G01N 35/04* (2013.01); *H05B 6/108* (2013.01); *B01L 3/50851* (2013.01); *B01L 9/06* (2013.01); *B01L 2200/147* (2013.01); *B01L 2300/0654* (2013.01); *B01L 2300/0803* (2013.01); *B01L 2300/0806* (2013.01); *B01L 2300/0841* (2013.01); *B01L 2300/12* (2013.01); *B01L 2300/1811* (2013.01); *B01L 2300/1894* (2013.01); *G01N 2035/0444* (2013.01)

(56) References Cited

U.S. PATENT DOCUMENTS

| | | | |
|---|---|---|---|
| 2004/0129555 A1* | 7/2004 | Marchitto | B01J 3/08 204/157.15 |
| 2005/0064582 A1* | 3/2005 | Wittwer | B01L 3/5082 435/287.2 |
| 2005/0158725 A1 | 7/2005 | Yukimasa et al. | |
| 2008/0308160 A1 | 12/2008 | Boege et al. | |
| 2009/0082219 A1* | 3/2009 | Ermantraut | B01L 3/5027 506/10 |
| 2013/0101983 A1* | 4/2013 | Chandra | B01L 7/52 435/3 |
| 2013/0157276 A1* | 6/2013 | Edvinsson | B01L 7/52 435/6.12 |
| 2013/0260421 A1* | 10/2013 | Yamaguchi | B01L 7/52 435/91.2 |
| 2016/0289736 A1 | 10/2016 | Jones et al. | |

FOREIGN PATENT DOCUMENTS

| | | |
|---|---|---|
| EP | 2 095 877 | 9/2009 |
| JP | 2006-122041 | 5/2006 |
| JP | 2013-524790 | 6/2013 |
| WO | WO 98/49340 | 11/1998 |
| WO | 2011/130785 | 10/2011 |
| WO | WO 11/135535 | 11/2011 |

OTHER PUBLICATIONS

Pal, D. et al., "A portable battery-operated chip thermocycler based on induction heating", Sensors and Actuators A, 2002, vol. 102, pp. 151-156.
International Search Report issued in International (PCT) Application No. PCT/AU2014/000983, dated Dec. 11, 2014.
International Preliminary Report on Patentability issued in International (PCT) Application No. PCT/AU2014/000983, dated Sep. 25, 2015.
Extended European Search Report dated May 22, 2017 in corresponding European Application No. 14854248.3.
Pal et al., "A power-efficient thermocycler based on induction heating for DNA amplification by polymerase chain reaction", Review of Scientific Instruments, 75(9):2880-2883 (2004).
Chinese Office Action dated Jul. 4, 2018 in Chinese Application No. 201480067694.9 with Machine Translation.
Russian Office Action dated Jun. 18, 2018 in corresponding Russian Application No. 2016117135/05 with Machine Translation.
Japanese Office Action dated Jul. 26, 2018 in corresponding Japanese Application No. 2016-524516 with English Translation.
European communication dated Jun. 13, 2018 in corresponding European Application No. 14 854 248.3.

* cited by examiner

THERMOCYCLER

FIELD OF THE INVENTION

The present invention relates to an improved thermocycler, and will be described hereinafter with reference to this application. In particular, the improved thermocycler has been described herein for use in conducting nucleic acid amplification reactions. However, it will be appreciated that the invention is not limited to this particular field of use.

BACKGROUND OF THE INVENTION

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Systems which require multiple or cyclic chemical reactions to produce a desired product often require careful temperature control, and reproducible and accurate control over the time the reaction is held at temperature. Such reactions include, for example, nucleic acid amplification reactions such as the polymerase chain reaction (PCR) and the ligase chain reaction (LCR).

PCR is a technique involving multiple cycles that results in the geometric amplification of certain polynucleotide sequences each time a cycle is completed. The technique of PCR is well known and is described in many books, including, PCR: A Practical Approach, M. J. McPherson, et al., IRL Press (1991), PCR Protocols: A Guide to Methods and Applications by Innis, et al., Academic Press (1990), and PCR Technology: Principals and Applications for DNA Amplification H. A. Erlich, Stockton Press (1989). PCR is also described in many US patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584. The content of these documents is incorporated herein by reference in their entirety.

The PCR technique typically involves the step of denaturing a polynucleotide, followed by the step of annealing at least a pair of primer oligonucleotides to the denatured polynucleotide, i.e., hybridizing the primer to the denatured polynucleotide template. After the annealing step, an enzyme with polymerase activity catalyzes synthesis of a new polynucleotide strand that incorporates the primer oligonucleotide and uses the original denatured polynucleotide as a synthesis template. This series of steps (denaturation, primer annealing, and primer extension) constitutes a PCR cycle.

As cycles are repeated, the amount of newly synthesized polynucleotide increases geometrically because the newly synthesized polynucleotides from an earlier cycle can serve as templates for synthesis in subsequent cycles. Primer oligonucleotides are typically selected in pairs that can anneal to opposite strands of a given double-stranded polynucleotide sequence so that the region between the two annealing sites is amplified.

Denaturation of DNA typically takes place at around 90 to 95° C., annealing a primer to the denatured DNA is typically performed at around 40 to 60° C., and the step of extending the annealed primers with a polymerase is typically performed at around 70 to 75° C. Therefore, during a PCR cycle the temperature of the reaction mixture must be varied, and varied many times during a multicycle PCR experiment.

In order to speed up the overall analysis time, there is a need to be able to bring the reagents to the desired temperature quickly, and for the reaction to be uniformly held at temperature for a discrete amount of time before bringing the reaction to the next temperature in the cycle. There is also a need for accurate temperature control over the reactants.

A number of thermal "cyclers" used for DNA amplification and sequencing are disclosed in the prior art in which one or more temperature controlled elements or "blocks" hold the reaction mixture, and wherein the temperature of the block is varied over time. These devices suffer the drawback that they are slow in cycling the reaction mixtures and temperature control is less than ideal. In an effort to overcome the need to cyclically raise and lower the temperature of the heating blocks, others have devised apparatus known in the art as a thermocycler. In this apparatus, multiple temperature controlled blocks are kept at different desired temperatures and a robotic arm is utilized to move reaction mixtures from block to block. Typical thermocycler systems are disclosed in U.S. Pat. Nos. 5,443,791; 5,656,493 and 6,656,724. However, as will be appreciated, these systems suffer from their own set of drawbacks. For example, they have a relatively limited throughput, they are physically large, prone to break down, expensive and require constant routine maintenance.

Various attempts have been made in the prior art to reduce the overall cycle time and/or improve temperature control, and generally address the above-mentioned disadvantages. The most common methods are non-contact and rely on hot air cycling, which is carried out by rapidly switching streams of air at the desired temperature. However the control and application of hot air is not efficient or readily controllable.

An advance over such prior art devices was first disclosed in International PCT Publication No. WO 98/49340, which teaches a thermocycler using a rotatable platform for amplification and detection of DNA fragments. Reagents are loaded into the loading wells of the rotatable platform, and upon rotation of the platform are mixed together and centrifugally displaced into the reaction wells, which are distributed about the periphery of the platform. The rotatable platform is then thermally cycled. By rotating the platform the individual reaction wells can be continuously monitored by a fixed detector. Thermal cycling of the platform is effected with conventional heating methods, such as by use of a heating element to heat a stream of air which is directed at the platform. The disadvantage of heating the entire platform with hot air is that the surrounding structures in the device will also become heated, which will need to be cooled in the cooling phase of the cycle otherwise they will continue to radiate heat and will affect the temperature of the reactions occurring in the reaction wells. Heating and cooling parts of the device other than the platform itself is inefficient, and temperature control using a stream of heated air is less than ideal. Also, it is difficult to measure the temperature of the reaction mixture, which therefore needs to be estimated. Because the temperature differential between air and the reaction mixture is very large, the estimated reaction temperature is subject to very large errors, meaning that there is poor temperature control.

Other methods of heating disclosed in WO 98/49340 comprise directing a narrow beam of IR light or microwave energy at a portion of the platform and then rotating the platform through or past the beam. In this way, each portion of the platform is effectively "pulsed" with energy, and as such only a small portion of the platform is heated at any one time. This can lead to a thermal differential across the platform. In WO 98/49340, the platform is cooled by exposing the rotatable platform to a stream of coolant fluid, such as ambient air, which is optionally chilled. In summary, the heating methods employ non-coherent and non-focused sources of electromagnetic energy, which require high power for the reaction wells to reach the required temperature. Additionally, heating the reactions via these conventional means can take minutes to reach the predetermined set-point temperature.

In light of forgoing discussion, it is a preferred object of the present invention to develop a non-contact real-time thermocycler which has improved thermal cycling speed and which therefore reduces the overall cycle time.

It is an object of the present invention to overcome or ameliorate one or more of the disadvantages of the prior art, or at least to provide a useful alternative.

SUMMARY OF THE INVENTION

The present invention relates to a high-speed thermal cycler (thermocycler) that uses a source of electromagnetic energy (EM) to heat a rotatable platform. The apparatus also provides excellent temperature control over the reaction. Preferably the electromagnetic energy is radio-frequency (RF) energy (between around 3 kHz to 300 GHz), and in one embodiment is RF energy at 50-60 kHz. In a preferred embodiment, the source of electromagnetic energy is an inductor and the rotatable platform is formed from a material which is adapted to be inductively heated when exposed to said inductor, or is in thermal communication with a material which is adapted to be inductively heated when exposed to said inductor. Preferably the rotatable platform has a plurality of reaction wells for containing the PCR reagents, or is adapted to contain a corresponding plurality of reaction/sample containers for containing, say, PCR reagents. Each reaction container is in thermal communication with the reaction well and the rotatable platform. The inductor surrounds a sufficient amount of the rotatable platform in order to heat the entire platform simultaneously, uniformly, and at high speed, irrespective of whether the platform is rotated or the speed of rotation. In one preferred embodiment, the inductor is shaped as a ring and completely surrounds the rotatable platform. This embodiment is particularly advantageous if the platform rotational speed is relatively slow or zero, as the entire platform is simultaneously heated. In another embodiment, if the speed of platform rotation is required to be relatively high, the inductor may not completely surround the platform and yet may still heat the entire platform substantially simultaneously, although the inductor surrounds a sufficient amount of the rotatable platform in order to heat the entire platform simultaneously, uniformly, and at high speed. There are various advantages which this configuration provides, as will be discussed further below.

According to a first aspect, the present invention provides a thermocycler comprising:
a rotatable platform having a plurality of reaction wells, wherein the rotatable platform is adapted to be inductively heated by exposure to electromagnetic energy; and
an electromagnetic energy source adapted to direct electromagnetic energy at the rotatable platform,
wherein the electromagnetic energy source surrounds a sufficient amount of the rotatable platform in order to heat the platform substantially simultaneously.

Preferably the rotatable platform and/or the reaction wells are formed, at least in part, of a material which is adapted to be inductively heated by exposure to electromagnetic energy. In alternative embodiments, the rotatable platform and/or the reaction wells are in thermal communication with a material which is formed, at least in part, of a material which is adapted to be inductively heated by exposure to electromagnetic energy. These embodiments will be discussed further below.

Preferably the reaction wells are distributed about the periphery of the platform, which is annular in shape. However, other arrangements will be understood by the skilled person. It will be appreciated that the entire platform is heated substantially simultaneously.

In some preferred embodiments, the reaction wells are separately formed but in thermal contact with the rotatable platform, and in other embodiments the reaction wells are integrally formed with the rotatable platform and as such are formed from the same material. In these embodiments the material is adapted to be inductively heated by exposure to electromagnetic energy. In some embodiments, the reaction wells are connected together with one or more flanges in a circular array to provide the rotatable platform.

In some embodiments, the rotatable platform is adapted to contain or receive a plurality of reaction containers in the reaction wells. In one embodiment, each reaction container is formed, at least in part, of a material which adapted to be inductively heated in response to being exposed to electromagnetic energy. In other embodiments, both the platform and the reaction wells are formed, at least in part, of a material which is adapted to be inductively heated in response to being exposed to electromagnetic energy, and the reaction containers are formed from a highly thermally conductive material.

Preferably the apparatus further comprises a drive system adapted to rotate the rotatable platform about an axis of rotation. Preferably the apparatus further comprises a control unit to rotate the rotatable platform at a predetermined controllable user-selectable rotational speed.

Preferably the platform and the reaction wells and/or the reaction containers are formed from a material which absorbs electromagnetic energy and converts the absorbed electromagnetic energy into thermal energy. Preferably the platform and/or the reaction containers are formed from a material which is chosen such that it can absorb electromagnetic energy generated and delivered by the electromagnetic energy source at a sufficient rate to heat the platform at a predetermined rate, and thereby heat the reagents contained in the reaction wells/reaction containers. Preferably the platform is formed from a material having a sufficient thermal conductivity such that the temperature across the platform is uniform during heating. High thermal conductivity is preferred to ensure uniform temperatures within the reactants or reagents contained within the reaction wells or reaction containers. In preferred embodiments, the mass of the rotatable platform is minimised to minimise the induction energy required to bring the platform to the predetermined temperature.

Some suitable materials for the platform and/or the reaction wells/containers are conductive metals which are magnetic or non-magnetic. Suitable materials include, but are not limited to: steel, carbon, tin, tungsten, aluminium, copper, gold, brass and combinations thereof. In an alternative or an additional embodiment, the rotatable platform can be inductively heated indirectly by attaching a susceptor into thermal contact with the rotatable platform. In this embodiment the susceptor is formed from a conductive material, which may or may not be magnetic, and the platform is formed from highly conductive material. As the skilled person would understand, it is also possible to inductively heat a material even if it is not electrically conductive through magnetic hysteresis losses. In this embodiment, the material is chosen to have significant relative permeability, i.e. the measure of the ability of a material to support the formation of a magnetic field within itself, or in other words, the degree of magnetization that a material obtains in response to an applied magnetic field. Suitable materials are chosen from cobalt-iron, permalloy, electrical steel, ferritic stainless steel, martensitic stainless steel, ferrite (nickel zinc), carbon steel, nickel and combinations thereof. Other suitable materials will be known to the skilled person. Magnetic hysteresis causes internal friction which in turn produces heat, and is caused when magnetic parts pass through the inductor. Magnetic materials naturally offer electrical resistance to the rapidly changing magnetic fields within the inductor.

Preferably the rotatable platform and its associated reaction wells are formed from aluminium, and the platform is preferably rotated so that the reaction samples in the reaction wells (or reaction containers) are rotated past a single optical detection unit to detect an optical signal from within the reaction occurring in the reaction wells/containers, and thereby monitor progress of the reactions. The rotatable platform may be heated rapidly, at about 15° C. per second, and is preferably cooled with a forced jet of ambient or chilled air (2-5° C.), although other methods of cooling will be known to the skilled person.

Preferably the electromagnetic energy source completely surrounds the rotatable platform. Preferably the electromagnetic energy source does not deliver thermal energy to the rotatable platform by direct contact, but rather via indirect contact. Preferably the electromagnetic energy source provides electromagnetic energy continuously or intermittently based on a variety of factors, e.g. the desired temperature of the reagent(s) in the reaction wells or reaction containers, the rate at which thermal energy is removed from the reaction wells or reaction containers, the desired rate of temperature change, etc. The intermittent energy delivery may be via pulses of energy, which may be the same or different duration, or may be pulses of long, then short duration, or tailored as required to achieve a predetermined temperature. The intermittent electromagnetic energy which is delivered may be delivered according to a predetermined schedule, which is determined from an initial calibration routine.

Preferably the electromagnetic energy source is an inductor and is magnetically coupled to the rotatable platform and associated reaction wells to induce a current therein and to generate heat. It will be appreciated that having the electromagnetic energy source substantially surround the rotatable platform enables the entire platform to be evenly heated at a relatively fast rate. Alternatively, the rotatable platform includes a susceptor in thermal contact with the reaction wells or reaction containers, wherein the inductor is coupled to the susceptor to induce a current therein and generate heat within the platform and reaction wells/reaction containers. Preferably the inductor is magnetically coupled to the susceptor.

The relevant prior art which teaches the use of a rotatable platform in thermal cycling apparatus only teaches heating a portion of a platform at any one time, for example by directing infra red (IR) light at a portion of the platform and then rotating the platform past or through the light. Each portion of the platform is effectively 'pulsed' with energy. Alternatively, a laser emitting visible or IR light, or a microwave source is directed at a reaction well or a reaction container which is heated as it is rotated past the energy source. In these examples, as the heating source is effectively a "point source", the platform must be rotated past or through the point source in order to heat the platform and each reaction container/well uniformly. Other examples in the prior art use a magnet positioned adjacent to the rotatable platform, wherein rotation of the platform past the magnet and through the magnetic field induces the generation of heat within the platform. In other prior art examples, a pair of mutually opposed magnets is provided and the platform rotated within the gap between the magnets to induce the generation of heat within the platform. In all these cases, only a small portion of the platform is heated at any one time and therefore the platform must be rotated past the heating point source in order to heat the entire platform. The need to rotate the platform to heat the platform uniformly limits the degree of control over the speed of rotation, which is important in certain embodiments and applications. The present invention is an advance over the prior art in that the speed of rotation can be decoupled from the ability to heat the platform uniformly and at high speed.

Furthermore, the relevant prior art teaches the use of a single thermal source for heating a small portion of the platform, wherein the source is mounted below the platform to provide unidirectional heat in a substantially upward direction towards the platform. The thermal source may alternatively be mounted above the platform. In this prior art, the unidirectional external heating causes temperature differentials within and across the platform, requiring additional time for the temperature to equalise across the platform. As such, a need exists to heat the platform uniformly to more accurately control the temperature of the reagents held within the wells. The present invention is an advance over the prior art in that an electromagnetic (EM) energy source is adapted to inductively heat the platform simultaneously and from within, allowing substantially uniform heating of the entire platform and/or chambers/wells. As the induction heat is supplied to heat the platform substantially simultaneously, temperature differentials are minimised or eliminated, allowing the reactions to occur in less time.

In other embodiments of the present invention, a combination of an inductor and a point heating source are contemplated, such as a laser emitting visible or IR light, or a microwave source is directed at the rotatable platform. This embodiment combines prior art "point source" heating of the platform (pulsed energy delivery) with the present invention, in which the entire rotatable platform is heated substantially simultaneously.

As discussed above, the present invention enables the factor of speed of rotation of the platform to be decoupled from the ability to heat the platform. The entire platform can be heated evenly without the platform being rotated, or whilst it is being rotated slowly. This aspect is an advance over the prior art, since the speed of rotation can be used to control the centrifugal forces, and therefore control the movement of fluids on and about the platform.

In contrast to the prior art, the present invention can be considered to be a transformer. A varying/alternating current in the primary winding (the inductor) creates a varying magnetic flux in the transformer's core and thus a varying magnetic flux through the rotatable platform (the secondary winding) causing circulating electrical currents. The circulating (eddy) currents flow against the electrical resistivity of the metal, generating precise and localised heat without any direct contact between the rotatable platform and the primary winding. It will be appreciated that the secondary winding is a single short circuited turn.

The present invention not only serves to improve the rate at which the platform can be heated, and therefore reduce overall cycle times, but also improves the evenness of the heating across the platform, and therefore control over the chemical reactions occurring in the reaction wells or reaction containers. The applicant has found that control over the accuracy at which the platform can be heated, and the speed of heating of the platform, can reduce overall cycling times, which is an important aspect of commercially-available devices. In addition, because only the platform is heated, and no other surrounding parts of the device are heated, the device is energy efficient.

Preferably the thermocycler system of the invention heats the entire platform substantially simultaneously. Preferably the thermocycler is configured such that the temperature differential across the platform is kept below 10, 5, 4, 3, 2, 1, 0.5 or 0.1% during the heating phase and when the platform is at temperature. Preferably the temperature of the reagents in the reaction wells or reaction containers are uniform across the rotatable platform such that the maximum difference in temperature between any 2 portions of the platform, or within the reagents held within the reaction wells or reaction containers is less than 1, 0.75, 0.5, 0.2, 0.1 or 0.01° C. Preferably the electromagnetic energy source is an inductor which substantially surrounds the rotatable platform. In preferred embodiments the inductor completely surrounds the rotatable platform, but in other embodiments surrounds more than about 45, 50, 55, 60, 65, 70, 75, 80, 85, 90, 91, 92, 93, 94, 95, 96, 97, 98, or 99% of the total circumference of the rotatable platform. It will be appreciated that the inductor may be configured in 2 or more sections spanning portions of the circumference of the rotatable platform, however the combination of the sections add up to greater than 45, 50, 55, 60, 65, 70, 75, 80, 85, 90, 91, 92, 93, 94, 95, 96, 97, 98, or 99% of the total circumference of the rotatable platform.

In preferred embodiments, the electromagnetic radiation is delivered at a frequency of between 35-45 kHz or between 50-60 kHz, i.e. radio frequency. However, in other embodiments the radiation is between 5 kHz and 100 MHz. In contrast, some prior art devices teach the use of electromagnetic energy in the IR and visible frequency range, which is between 300 GHz to 430 THz.

The coolant gas can be any of a large number of gasses, however, for the sake of convenience and cost effectiveness, in most cases the coolant gas will simply be air at ambient temperature. It is, however, possible that in some situations refrigerated air may be used. This may be particularly beneficial where, after the required number of cycles have been conducted, it is desirous to cool the samples to sub-ambient temperatures.

Denaturation of DNA typically takes place at around 90 to 95° C., annealing a primer to the denatured DNA is typically performed at around 40 to 60° C., and the step of extending the annealed primers with a polymerase is typically performed at around 70 to 75° C. Therefore, during a PCR cycle the temperature of the reaction mixture must be varied, and varied many times during a multicycle PCR experiment. The apparatus of the present invention enables the reagents held within the reaction wells or reaction containers to be heated at rates of 0.1, 0.2, 0.3, 0.4, 0.5, 0.6, 0.7, 0.8, 0.9, 1, 2, 3, 4, 5, 10, 15, 20, 25, and in some cases 30° C./second. It will be appreciated that even higher rates of heating are possible depending on the amount of power delivered to the inductor from the electromagnetic energy source and the choice of materials. The rotatable platform can be cooled at rates of 1, 2, 3, 4, 5, 6, 7, 8, 9, 10, 12, 15, and in some cases 20° C./second. The extremely fast heating rate, and the precise rate at which the rotatable platform can be heated, enables a reduced overall cycle time, which is a significant advantage for commercial devices.

The present invention additionally employs a thermocouple or thermistor in thermal contact with the rotatable platform, in order to directly measure the temperature of the rotatable platform and/or the reaction containers/wells, and therefore the reagent(s) held within the reaction containers/wells in real time. In this way, additional control over the reaction temperature is possible, especially in being able to bring the reaction to temperature and then precisely hold the reaction at temperature for a predetermined time. In this way, there is no need to have longer-than-necessary hold times, which further reduces the overall cycle time. Additionally, there is improved control over the reaction temperature as the temperature differential between the reaction container and the platform is less than the temperature differential between the reaction container and heated air of prior art devices. This enables more accurate temperature modelling of the reaction container and thus the reactants contained within the container.

Real-time monitoring of the rotatable platform temperature means that the control software can fine tune the amount of energy being delivered to the inductor, and therefore how fast the rotatable platform can be heated. In some cases, it is preferable to deliver relatively high power to the primary winding to cause the platform to heat very quickly, and then control the temperature at a set point by continuously adjusting the power level to the primary winding. In other preferred embodiments it is possible to heat the platform whilst simultaneously admitting coolant gas, and by fine tuning the amount of energy delivered to the primary winding it is possible to bring the rotatable platform to the required temperature faster than prior art devices. As the entire platform is heated simultaneously, or substantially simultaneously, this level of control is not possible with prior art "point source" methods of heating discussed above.

The thermocycler of the invention is particularly adapted for use in nucleic acid amplification reactions such as the polymerase chain reaction (PCR) and the ligase chain reaction (LCR). However, it will be appreciated that the apparatus can be used in a wide variety of systems which require multiple or cyclic chemical reactions to produce a desired product. In relation to PCR, preferably the sample to be analysed or reacted is a nucleic acid such as DNA or RNA containing sample. Other components of the sample will typically include oligonucleotide primers, deoxyadenosine triphosphate (dATP), deoxycytidine triphosphate (dCTP), deoxyguanosine triphosphate (dGTP), deoxythymidine triphosphate (dTTP), and at least one of a thermostable DNA polymerase, enzymatically active fragments thereof, an enzymatically active derivative thereof and a reverse transcriptase.

Preferably the time the sample is maintained at the predetermined temperature is pre-selectable and controllable. In an embodiment of the invention which makes use of the thermocycler for nucleic acid amplification, the thermal cycling is sufficient such that the following reactions take place:
  (a) denaturation of the DNA into its component strands;
  (b) annealing of the oligonucleotide primers to complementary sequences in the DNA; and
  (c) synthesis of new DNA strands;

Preferably these steps are repeated until a desired level of amplification has been achieved. The thermocycler may also include a thermal cycle which is suitable for denaturing the sample, wherein the sample is typically denatured for between about 2 to 10 seconds.

It can be seen from the above discussion that the device of the present invention will enable the rapid cycling between the temperatures routinely used in carrying out the polymerase chain reaction and other enzymatic reactions. The use of the device of the present invention will, therefore, provide an effective method of cycling a reaction mixture between various temperatures.

In yet a further preferred embodiment of the present invention monitoring means to assess the progress of the reaction occurring in the reaction wells or reaction containers is provided. Typically, this monitoring means will be a fluorescence detector, spectrophotometer, or photometer. This is particularly useful in monitoring the progress of a number of enzymatic reactions where a change in optical density or fluorescence of the product is observed. Such monitoring means is very useful in monitoring PCR reactions. In this case an intercalating dye, such as ethidium bromide or SYBR® Green, would be added to the reaction mix. When the dye binds to double stranded DNA there is fluorescence. Accordingly, by monitoring the degree of fluorescence in the reaction mixture an assessment as to the number of doublings which have occurred can be made. Alternatively, fluorescently labelled probes that hybridize to the DNA could be used. Other methods would be known to the skilled person.

The skilled person would understand that cycling between various predetermined temperatures can be automated. This would involve one or more of: actuation of the inductor, turning off or pulsing the inductor, increasing the speed of the rotatable platform, decreasing the speed of the rotatable platform, holding the rotational speed of the platform constant, reducing the rotational speed of the platform to zero or near zero, admitting coolant gas to cool the platform, reducing the flow of coolant gas to zero, controlling the temperature of the platform to a predetermined temperature, changing the platform temperature from one predetermined temperature to another (either colder to hotter, or vice versa), etc. Further, in the situation where monitoring means are provided and the reaction has reached a suitable point, refrigerated gas may be pumped into the chamber thereby cooling the reaction mixture to a sub-ambient temperature.

In one embodiment, the rotatable platform is removable from the device, but in other embodiments the platform is fixedly mounted within the device. In one embodiment, the reagents or reactants are introduced into the reaction wells, and thermally cycled. In this case, there is no requirement for the reaction containers. However, in an alternative embodiment, reaction containers are loaded into the reaction wells, which are adapted to receive the reaction containers. The reagents or reactants are introduced into the reaction containers, and thermally cycled.

In a first embodiment of a rotatable platform suitable for use in the apparatus of the invention, the platform is formed from aluminium and is configured to hold 48 reaction containers. However, it will be appreciated that the platform can be configured to hold fewer or more than 48 of the reaction containers as required, such as 96, 192 or 384 reaction containers. It will be appreciated that the platform can be configured with any number of reaction containers/wells as required and to suit the desired application. The platform is preferably configured as a circular array of sleeves for holding corresponding reaction containers, wherein the sleeve is the reaction well. The sleeve is adapted to hold the container therein. In one embodiment, the sleeves are angled at about 80 degrees from the horizontal and have an open aperture in the base of the sleeve in order for the optical detection apparatus to optically monitor a reaction occurring in the reaction tube held within the sleeve. The material of construction of the reaction container is chosen to be optically transparent at the wavelength(s) of light at which the optical detection apparatus operates. The sleeves can be angled at any angle from as low as 30 degrees from horizontal, to vertical. The platform also preferably includes one or more temperature sensors within it to accurately measure the temperature of the aluminium.

In some preferred embodiments, the rotatable platform is constructed to have a minimal mass such that the reaction containers insert into the reaction wells only to the level of the maximum fluid volume of the reaction container. In some embodiments, the maximum fluid volume is 5, 10, 15, 20, 25, 30, 40, 50, 60, 70, 80, 90, 100, 125, 150, 175, 200, 250, 300, 400, 500 or 1000 µL, and the thickness and diameter of the reaction well is adapted to suit the reaction container, which is chosen such that the maximum fluid height of the reaction container coincides with the upper surface of the reaction wells. In other words, the entire reaction container does not need to be heated/cooled—only the portion of it that contains the reactants. The portion of the reaction container that is above the maximum fluid volume does not need to be in contact with the rotatable platform or reaction well. This enables the speed of the device to be increased even further as time and energy is not wasted heating/cooling parts of the reaction container not in contact with the reagent/reactants. In this case, in the event that condensation forms inside the unheated upper portion of the reaction container, after each heating cycle the rotational speed of the platform can be increased sufficiently to ensure any condensation is drawn back down towards the base of the reaction container and into the main portion of reagents. In some embodiments, the platform speed can be increased to greater than 1500 rpm to centrifugally urge the condensate back to the base of the reaction container, for example as high as 3000 rpm. Other rotational speeds will be known to the skilled person.

In a second embodiment of a rotatable platform for use in the apparatus of the invention, the platform is formed from a plastics material which is optically transparent at the wavelength of light at which the optical detection apparatus operates. The platform is preferably around 130 mm in diameter and 1 mm thick, and is in effect a thin circular plate. The plate comprises radially inner loading wells and radially outer reaction wells, each of the wells being connected by a constricted passage. The constricted passage is adapted or configured such that fluid will flow from the inner to the outer wells only upon sufficient rotation of the platform (sufficient centrifugal force being generated). Each radially inner loading well is connected to one or more radially outer reaction wells by the passage. The reaction wells preferably have a diameter of about 6 mm, and are 'loaded' centrifugally via the loading wells. It will be appreciated that a first reagent can be loaded into the radially inner loading wells and a second reagent loaded into the radially outer reaction wells, and upon centrifugation, the first reagent is brought into contact with the second reagent. In this embodiment, the plate is sandwiched between one or more flat susceptors that are preferably of equal mass. The susceptor(s) may be aluminium discs. The bottom disc is "fixed" and rotatable within the apparatus, whereas the top disc is removable to allow a user to access the loading and reaction wells. The fixed aluminium disc has a spinning thermal sensor mounted within it to accurately measure its temperature. The top removable aluminium disc is identical in mass to the fixed aluminium disc so that it absorbs the same inducted energy as the fixed disc. It will be appreciated that the aluminium could be substituted for a different material adapted to be inductively heated. The temperature of the actual fluid in the reaction well can be modelled and controlled accurately. By utilising the top disc and optionally the lower fixed disc (or vice versa), which are inductively heatable, the plate is adapted to be heated from the top and the bottom surface simultaneously, to provide a very fast increase in temperature of the reagents/reactants in the reaction/loading wells. In an alternative embodiment, the system could operate with just the lower fixed disc being formed from aluminium and the top disc being selected from a plastics material. However, the rate of temperature rise would be slightly less than compared to both discs being formed from aluminium. In an alternative, embodiment the platform is formed from a material adapted to be inductively heated.

As discussed above, the rotatable platform is preferably formed from aluminium, or is formed from a plastics material and has a susceptor in thermal contact therewith, such that the platform is heatable in response to being exposed to electromagnetic energy, which is preferably RF energy. In an alternative, or an additional embodiment, the rotatable platform is formed from a plastics material having at least one filler that improves thermal conductivity. Such thermally conductive polymers can provide thermal conductivities from 2 W/mK (similar to glass) to 100 W/mK (similar to cast aluminium), whereas standard polypropylene is typically around 0.2 W/mK. A variety of fillers can be used, which are typically based on carbon or graphite, or nitrides such as aluminium and/or boron. Other fillers will be known to the skilled person. Use of high thermal conductivity polymers assists in providing uniform heating and delivering heat faster to the reagents, as the reagent in this embodiment are in direct contact with the thermally conductive plastic.

In a related embodiment, the filler is ferromagnetic particles. The resulting plastic platform can be heated when placed in an induction field via hysteresis losses, thereby heating the rotatable platform directly. In this embodiment, heating rates of 5 to 20° C./sec are possible.

In yet a further related embodiment, the present invention provides a system that eliminates the use of the two aluminium discs sandwiching the rotatable plate by molding the disc with fillers that improve thermal conductivity and allowing it to be heated inductively. By molding the disc in this way, the well shape and size can be optimised for heating and overall disc size. An additional advantage is that only a small viewing aperture is required for the optics, further improving the heat transfer, as all the other sides of the reaction well can be heated simultaneously.

The embodiments above provide uniform heating as the ferromagnetic particles are uniformly distributed throughout the rotatable platform. However, in these embodiments an alternative temperature sensing method is required. The skilled person would understand what options would be available, for example a thermistor could be moulded inside the rotatable platform.

According to a second aspect the present invention comprises a method of cycling a reaction mixture between predetermined temperatures, the method comprising the steps of:
providing the thermocycler according to the first aspect;
providing said reaction mixture in one or more of the reaction wells, and
cyclically:
actuating the inductor to heat the reaction wells and thereby heat the reaction mixture to a first predetermined temperature, and
contacting the rotatable platform with coolant fluid to cool the reaction mixture to a second predetermined temperature, different from the first predetermined temperature,
thereby thermally cycling the reaction mixture.

It will be appreciated that the reaction mixture can alternatively be contained in a reaction container which is held within the reaction well.

The method further comprises the step of actuating the inductor to cycle the reaction mixture (rotatable platform/reaction container(s)/reaction well(s)) between predetermined temperatures.

In preferred embodiments, prior to contacting the rotatable platform with coolant fluid the inductor is turned off or its power is reduced in order to cease or reduce heating the platform.

In a preferred embodiment, the present invention comprises a method of conducting nucleic acid amplification using the apparatus of the invention, wherein the polymerase chain reaction, ligase chain reaction or any other amplification technology is employed. Preferably the DNA is denatured into its component strands; oligonucleotide primers are annealed to complementary sequences in the DNA; and new DNA strands are synthesised. Preferably these steps are repeated until a desired level of amplification has been achieved.

The method comprises the steps of: loading the reaction mixture into the reaction well or a reaction container, and thermal cycling the reaction mixture until a desired level of amplification has been achieved. During the thermal cycling the reaction mixture is preferably monitored by a detection means.

Preferably the reaction wells are shaped and configured to hold a volume of fluid between 25 to 2500 µL, in particular 25, 50, 75, 100, 125, 150, 175, 200, 250, 300, 400, 500, 600, 700, 800, 900, 1250, 1500, 2000 or 2500 µL. The depth/height and diameter of the reaction well can be any value to suit the application. However, by way of example, well diameters of between 2 to 40 mm are possible, and well depths between 5 and 50 mm are desirable.

Any rotational speeds fall within the purview of the invention. However, by way of example, rotation speeds of 10, 50, 100, 150, 200, 300, 400, 500, 100, 1250, 1500, 1750, 200, 300, 400 or 5000 RPM are possible. If reagents are being dispensed into the reaction well/container, then rotational speeds between 10 and 500 RPM are preferred. Rotational speeds in excess of 1500 RPM may be required to urge condensation down into the main charge of reagents in the reaction well/container, for example speeds of 2000, 2500, 3000, 3500 or 4000 rpm. Preferably the platform is rotated at speeds between 500 and 1000 RPM when assaying the reaction mixture in the reaction well/containers.

According to a third aspect the present invention provides use of the thermocycler according to the invention to conduct a nucleic acid amplification reaction selected from the polymerase chain reaction (PCR) and the ligase chain reaction (LCR).

The skilled addressee will understand that the invention comprises the embodiments and features disclosed herein as well as all combinations and/or permeations of the disclosed embodiments and features.

BRIEF DESCRIPTION OF THE DRAWINGS

Preferred embodiments of the invention will now be described, by way of example only, with reference to the accompanying drawings in which.

DEFINITIONS

In describing and claiming the present invention, the following terminology will be used in accordance with the definitions set out below. It is also to be understood that the terminology used herein is for the purpose of describing particular embodiments of the invention only and is not intended to be limiting. Unless defined otherwise, all technical and scientific terms used herein have the same meaning as commonly understood by one having ordinary skill in the art to which the invention pertains.

Unless the context clearly requires otherwise, throughout the description and the claims, the words 'comprise', 'comprising', and the like are to be construed in an inclusive sense as opposed to an exclusive or exhaustive sense; that is to say, in the sense of 'including, but not limited to'.

Other than in the operating examples, or where otherwise indicated, all numbers expressing quantities of ingredients or reaction conditions used herein are to be understood as modified in all instances by the term 'about'. The examples are not intended to limit the scope of the invention. In what follows, or where otherwise indicated, % will mean 'weight %', 'ratio' will mean 'weight ratio' and 'parts' will mean 'weight parts'.

The terms 'predominantly' and 'substantially' as used herein shall mean comprising more than 50% by weight, unless otherwise indicated. The recitation of a numerical range using endpoints includes all numbers subsumed within that range (e.g., 1 to 5 includes 1, 1.5, 2, 2.75, 3, 3.80, 4, 5, etc.).

The terms 'preferred' and 'preferably' refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

PREFERRED EMBODIMENT OF THE INVENTION

The present invention will now be described with reference to the following examples which should be considered in all respects as illustrative and non-restrictive.

Figure 1:
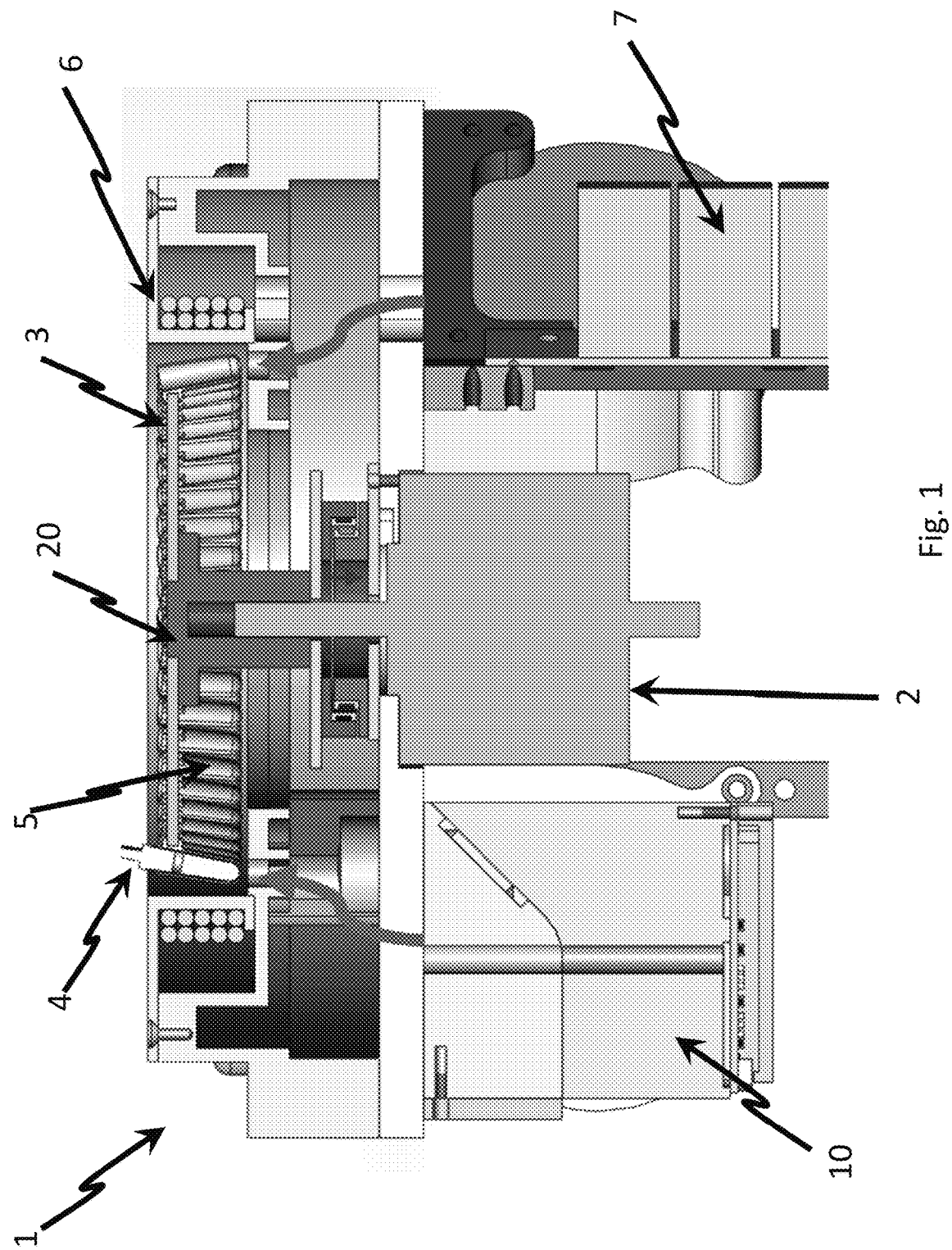
FIG. 1 is a side sectional view of apparatus according to the invention.

FIG. 1 shows a side sectional view of thermal cycler apparatus 1 according to the invention. The apparatus 1 comprises a drive motor 2 for rotating a rotatable platform 3 at a user-defined speed. The rotatable platform 3 is configured in a circular arrangement and is adapted to hold a plurality of plastic or glass reaction containers 4 in reaction wells 5. The rotatable platform is optionally releasably attachable to a stage 20 connected to the drive motor 2. Surrounding the rotatable platform 3 is an induction coil 6 for heating the entire rotatable platform 3 simultaneously, irrespective of whether the rotatable platform 3 is spinning or the speed of rotation. The induction coil 6 is preferably in the form of a ring.

The thermal cycler 1 of the invention is 'high-speed' in that it is capable of heating the rotatable platform 3 at a rate of at least 15° C. per second, and preferably 25° C./sec. The apparatus of the invention provides rapid energy transfer via inductive heating.

The configuration described above can best be described as a transformer, where the fixed induction coil 6 is the primary winding and the rotatable platform 3 is the secondary winding of the transformer that is effectively one turn that is a short circuit. The induction coil 6 also preferably includes a ferrite material (not shown) above and below it to better direct the magnetic flux into the rotatable platform 3.

The circuit used to generate the radio frequency (RF) energy (35-45 kHz or 50-60 kHz) to heat the reaction containers 4 in thermal contact with the reaction wells 5 and the rotatable platform 3 with inductive coupling is very similar to that as described in U.S. Pat. No. 6,046,442, which is incorporated in its entirety herein by reference. However, it will be appreciated that other circuit configurations can be employed.

In the embodiment shown in FIG. 1, a temperature sensor (not shown) is embedded in the rotatable platform 3 in order to directly monitor the temperature of the rotatable platform 3 during the thermal induction phase. The temperature data is transmitted via an infrared connection (not shown) to fixed electronics (not shown) within the housing of the thermal cycler apparatus 1. A thermal model of the reaction container 4 can be calculated so the temperature inside the container 4 can be accurately determined in real-time. In one non-limiting example, the thermal model is a 1st or 2nd order model relating reaction temperature to the temperature of the rotatable platform 3. The model constants can be varied depending on whether the rotatable platform is being heated or cooled. It will be appreciated that other mathematical models can be used to relate the reaction temperature to the temperature of the rotatable platform 3.

The thermal cycler apparatus 1 is also configured with a high velocity fan 7 for directing high velocity cooling fluid in the form of ambient air into the apparatus 1 which houses the rotational platform 3. The ambient air can be chilled prior to its introduction into the apparatus 1 in order to reduce the temperature of the reagents within the reaction containers 4 more rapidly.

The thermal cycler apparatus 1 is further configured with an optics detection module 10 to detect the progress of the reaction occurring in the reaction containers 4. The platform 3 is rotated so that the reaction containers 4 pass over a detection zone and the platform 3 is rotated at a sufficient speed such that each of the reaction containers 4 can be individually monitored.

It will be appreciated that the thermal cycler apparatus 1 as shown herein does not need to be rotated in order to inductively heat the rotatable platform 3, as the magnetic flux from the primary winding heats the entire rotatable platform 3 simultaneously, since it substantially surrounds the rotatable platform 3. The rotatable platform 3 is rotated in order to detect the course of the reactions in the reaction containers 4, and since there is a single optic detection module 10 each sample in a reaction container must be rotated past that point to detect an optical signal. The rotatable platform 3 may also be rotated in order to move fluids about on the platform and in order to commence, suspend or terminate a chemical reaction.

The rotatable platform 3 shown in FIG. 1 comprises a series of reaction wells 5 configured in a circular array, and includes an annular ring joined to the rotatable platform 3. The ring is formed from a thermally insulating material so that the only component being heated/cooled is the rotatable platform 3 and the reaction wells 5 and the reaction containers 4. Preferably the total mass being heated/cooled is kept to a minimum to maximise the heating/cooling rate.

Figure 2:
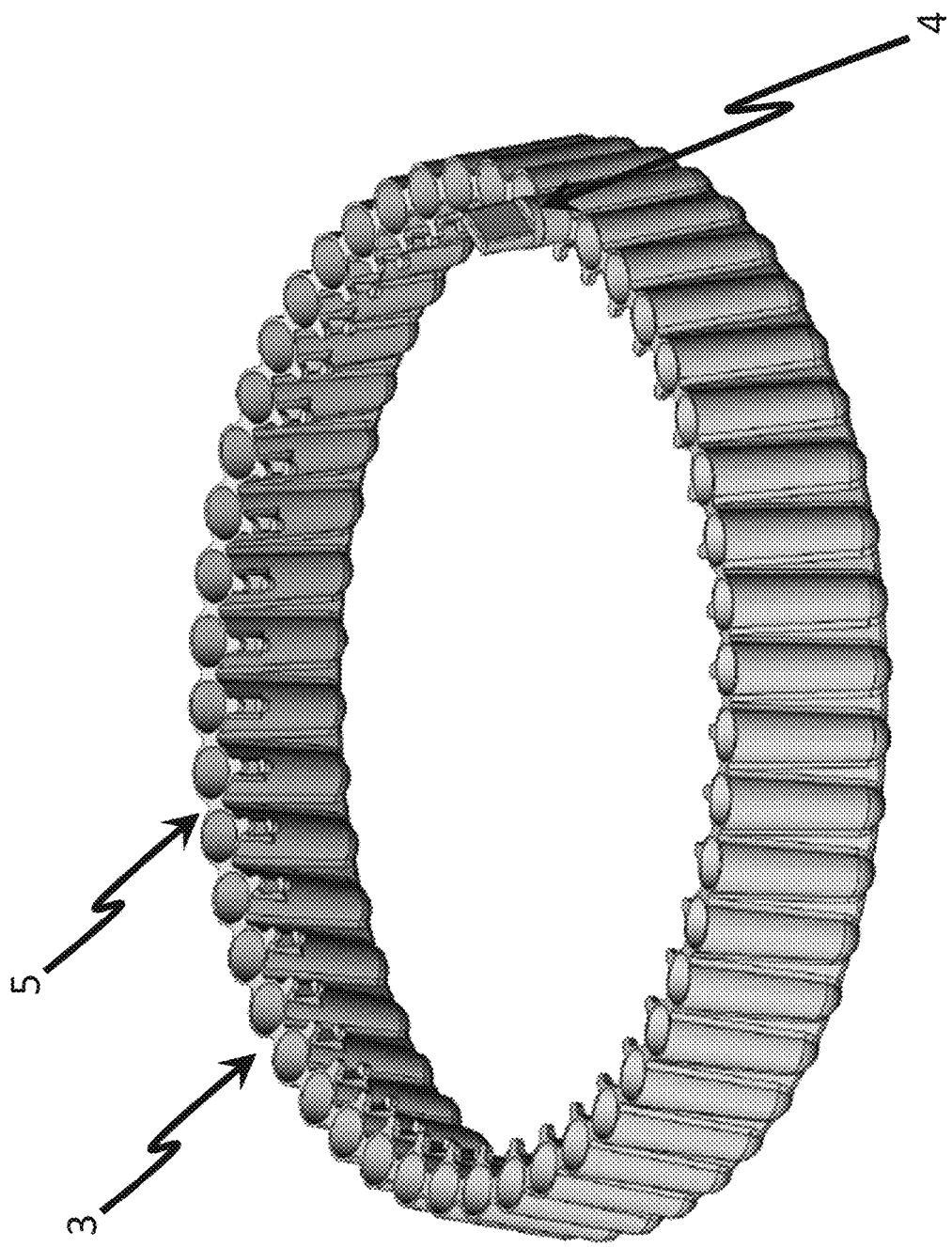
FIG. 2 is a perspective view of a rotatable platform suitable for use in the apparatus of FIG. 1.

FIG. 2 is a perspective view of a rotatable platform 3 suitable for use in the apparatus 1 of FIG. 1. The platform 3 is formed from aluminium and is configured to hold 48 reaction containers 4. However, it will be appreciated that the platform 3 can be configured to hold fewer or more than 48 of the reaction containers. Each of the reaction wells 5 are in the form of sleeves which are angled at about 80 degrees from the horizontal and has an open aperture in its base in order for the optical detection apparatus 10 to optically monitor the reaction occurring in the reaction containers 4 held within the sleeves. The material of construction of the reaction containers 4 is chosen to be optically transparent at the wavelength of light at which the optical detection apparatus 10 operates. The sleeves can be angled at any angle from as low as 30 degrees from horizontal, to vertical.

Figure 3:
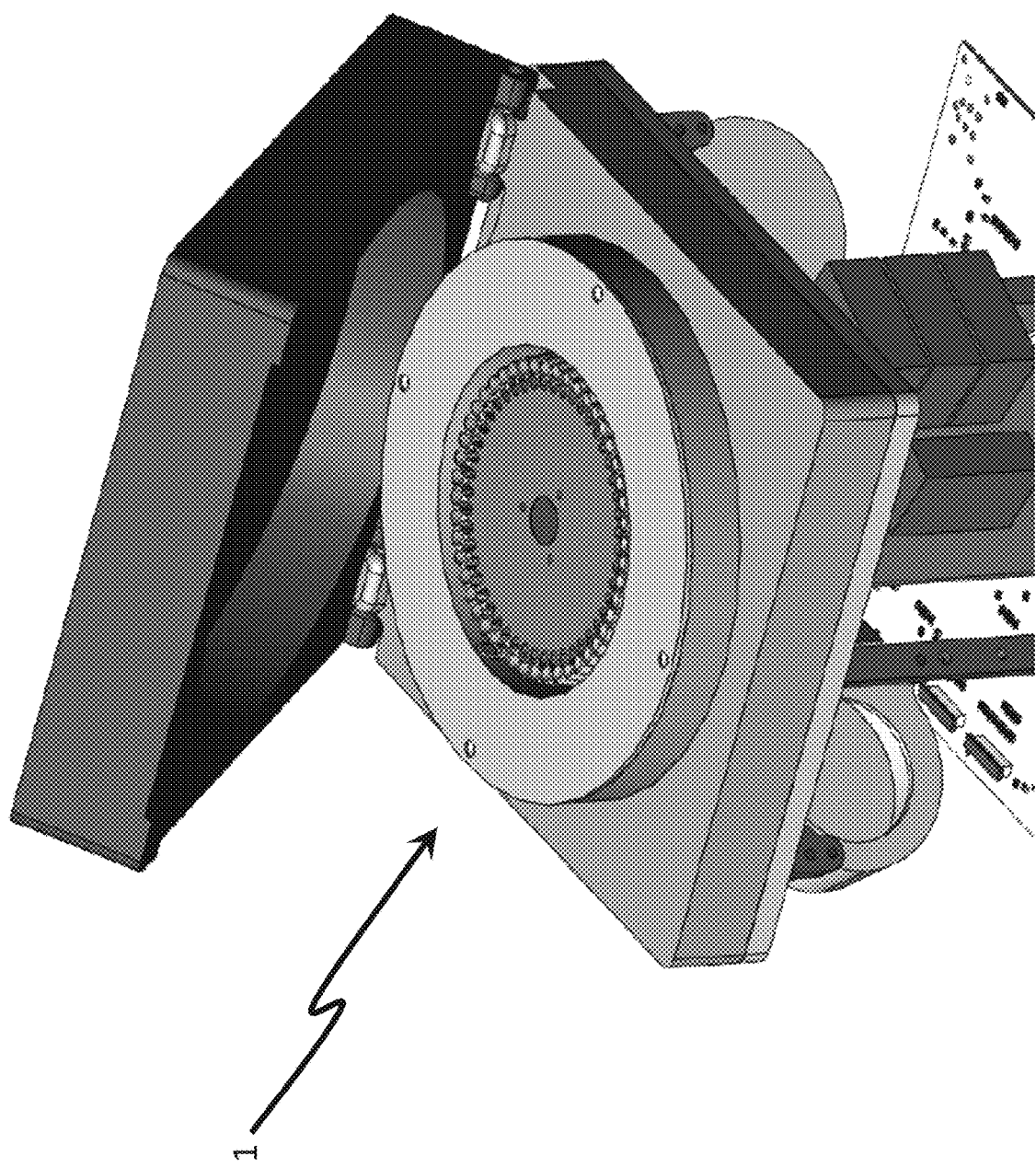
FIG. 3 is a perspective view of the apparatus according to FIG. 1 showing the lid in an open configuration in order to access the rotatable platform of FIG. 2.

FIG. 3 is a perspective view of the apparatus according to FIG. 1 showing the lid of the thermal cycler apparatus 1 in an open configuration in order to access the rotatable platform 3. The apparatus of the invention 1 also comprises a PC-based data acquisition and control system (not shown), in which a user can select a predetermined temperature cycling routine, rotation speeds, etc.

Figure 4:
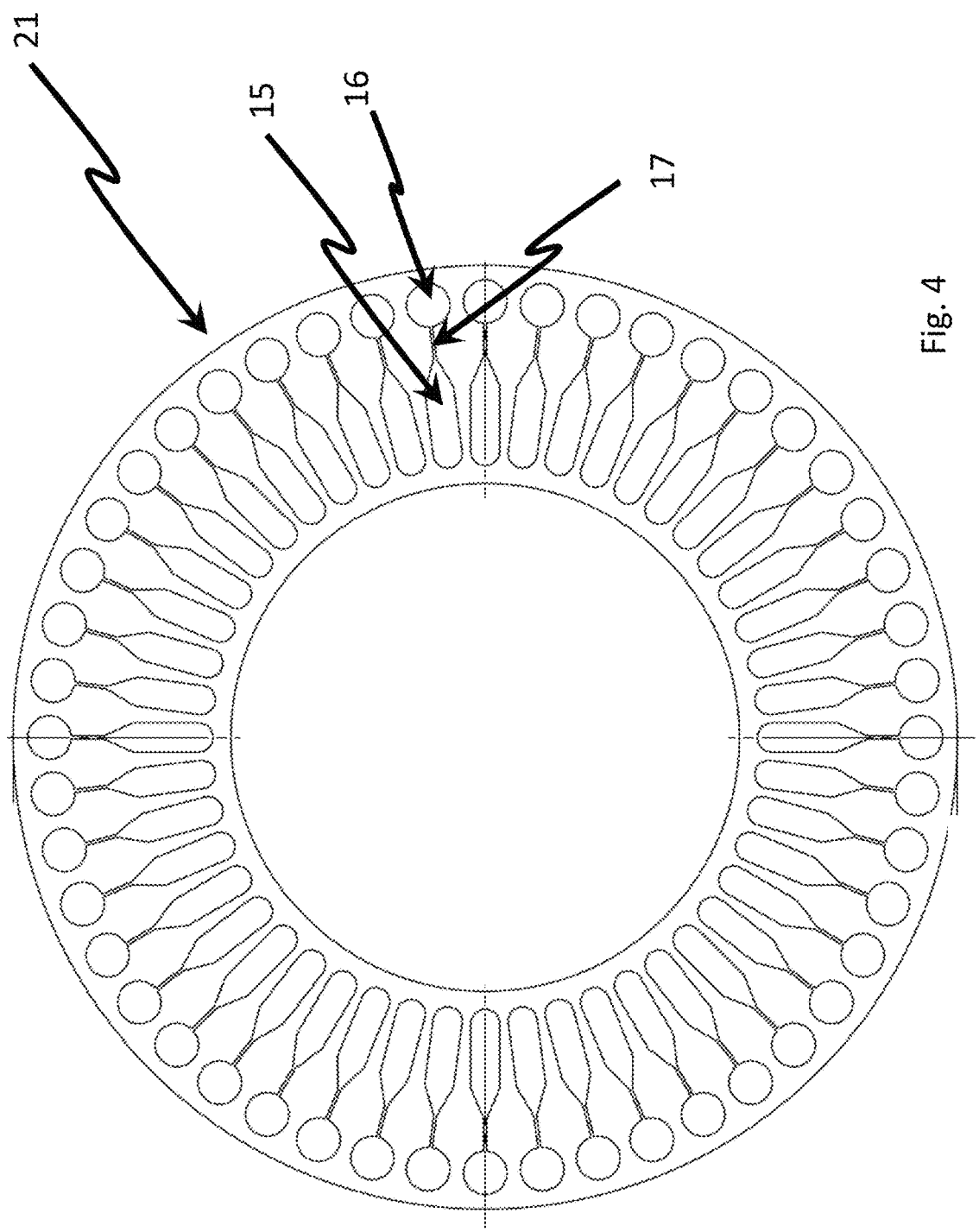
FIG. 4 is a plan view of an alternative rotatable platform for use in apparatus according to the invention.

FIG. 4 is a plan view of an alternative sample disc 21 for use in the apparatus 1 of the invention. In one embodiment the sample disc 21 is formed from a plastics material which is optically transparent at the wavelength of light at which the optical detection apparatus 10 operates. The sample disc 21 is around 130 mm in diameter and 1 mm thick, and is effectively a plate. The sample disc comprises radially inner loading wells 15 and radially outer reaction wells 16, which are connected by a constricted passage 17. The reaction wells 16 have a diameter of about 6 mm. The reaction wells 16 can be loaded centrifugally via the loading wells 15. It will be appreciated that a first reagent can be loaded into the radially inner loading wells 15 and a second reagent loaded into the radially outer reaction wells 16 and upon centrifugation the first reagent brought into contact with the second reagent. In an alternative embodiment, the sample disc 21 is formed, at least in part, of a material which adapted to be inductively heated in response to being exposed to electromagnetic energy.

In the example in FIG. 4, the flat rotatable sample disc 21 is sandwiched between a pair of flat aluminium discs (not shown) that are preferably of equal mass. The bottom disc is "fixed" and rotatable within the apparatus, whereas the top disc is removable to allow a user to access the wells 15 and 16. The fixed disc has a spinning thermal sensor mounted within it to measure the temperature of the fixed disc accurately. The top removable disc is identical in mass to the fixed disc so it absorbs the same inducted energy as the fixed disc. The temperature of the actual fluid in the reaction well 16 can be modelled and controlled accurately by controlling the energy output of the induction coil 6. By having the top disc and the lower fixed disc the sample disc 21 can be heated from the top and the bottom surface simultaneously, which will provide an even faster increase in temperature of the sample compared to the embodiment in FIG. 2. The unit could also operate, however, with just the lower fixed disc being formed from aluminium and the top disc being selected from a plastics material, however, the rate of temperature rise would be slightly less. In this example, the rotatable platform 3 is the combination of the lower aluminium disc and the sample disc 21, or the sample disc 21 if it is formed, at least in part, of a material which heatable in response to being exposed to electromagnetic energy.

In other embodiments, the rotatable platform 3 is formed from a plastics material or glass, and the reaction wells 5 are coated with a susceptor, or the rotatable platform 3 is formed from a plastics material and the reaction containers 4 are also formed from a plastics material which is coated with a susceptor. In further embodiments, the rotatable platform 3 is formed from a plastics material having at least one filler that improves thermal conductivity and allows it to be inductively heated. In other embodiments, the filler is ferromagnetic particles, which allows the plastic rotatable platform 3 to be heated when placed in an induction field via hysteresis losses, thereby heating the rotatable platform 3 directly.

Although the invention has been described with reference to specific examples, it will be appreciated by those skilled in the art that the invention may be embodied in many other forms. In particular features of any one of the various described examples may be provided in any combination in any of the other described examples.

The claims defining the invention are as follows:

1. A thermocycler comprising:
    a rotatable platform having a peripherally continuous conductor in the form of a ring and a plurality of reaction wells in electrical communication via the conductor, wherein the rotatable platform is adapted to be inductively heated by exposure to electromagnetic energy; and
    an inductor for directing electromagnetic energy at the rotatable platform,
    wherein the inductor is in the shape of a ring and completely surrounds the rotatable platform to thereby induce a current around the conductor in order to heat the entire platform substantially simultaneously.

2. The thermocycler according to claim 1 wherein the reaction wells are adapted to receive a corresponding plurality of reaction containers.

3. The thermocycler according to claim 2 wherein each reaction container is formed from a material which is adapted to be inductively heated by exposure to electromagnetic energy.

4. The thermocycler according to claim 3 wherein one or more of the reaction container is formed from a plastics material comprising ferromagnetic particles such that the container is inductively heatable.

5. The thermocycler according to claim 1 wherein the rotatable platform is circular and the plurality of reaction wells are distributed about the periphery of the platform.

6. The thermocycler according to claim 1 wherein the reaction wells are configured as an annular array of sleeves adapted to hold reaction containers.

7. The thermocycler according to claim 6 wherein the sleeves are angled at about 80 degrees from the horizontal and have an open aperture in the base of the sleeve to optically monitor a reaction occurring in the reaction container held within the sleeve.

8. The thermocycler according to claim 1 wherein the rotatable platform is formed from a material selected from: steel, carbon, tin, tungsten, aluminium, copper, gold, brass, cobalt-iron, permalloy, electrical steel, ferritic stainless steel, martensitic stainless steel, ferrite (nickel zinc), carbon steel, nickel and combinations thereof.

9. The thermocycler according to claim 1 wherein the platform and/or the reaction wells comprise a material having a sufficient thermal conductivity such that the temperature across the platform is substantially uniform during heating or cooling of the platform.

10. The thermocycler according to claim 1 wherein the electromagnetic energy is electromagnetic radiation delivered at a frequency of between 5 to 100kHz.

11. The thermocycler according to claim 1 wherein the inductor is configured to deliver continuous energy during a heating phase, or pulses of energy which may be the same duration or different durations.

12. The thermocycler according to claim 1 wherein the inductor is the primary winding in a transformer and the rotatable platform is the secondary winding, which is a single short circuited turn.

13. The thermocycler according to claim 1 wherein the thermocycler is configured such that the temperature differential across the platform is below 1% when the platform is at temperature, and/or wherein the temperature difference between any 2 portions of the platform, or within reagents held within the reaction wells or reaction containers is less than 1° C. when the platform is at temperature, and/or wherein the platform is inductively heatable at a rate of more than 15° C./second.

14. The thermocycler according to claim 1 further comprising a thermocouple or thermistor in thermal contact with the rotatable platform in order to directly measure the temperature of the rotatable platform and/or the reaction wells, and/or further comprising a drive system adapted to rotate the rotatable platform about an axis of rotation, and a control unit to rotate the rotatable platform at a predetermined controllable user-selectable rotational speed, and/or further comprising an optical detection unit to detect an optical signal from the reaction occurring in a reaction well/container, and thereby monitor progress of reactions in the reaction well/container, wherein the material of construction of a reaction container is chosen to be optically transparent at the wavelength(s) of light at which the optical detection apparatus operates.

15. The thermocycler according to claim 1 further comprising a cooling unit adapted to cool the platform with a cooling fluid.

16. The thermocycler according to claim 1 further comprising a point heating source selected from a laser emitting visible or IR light, or a microwave source.

17. The thermocycler according to claim 1 further comprising monitoring means to assess progress of a reaction occurring in the reaction wells or a reaction container, wherein the monitoring means is a fluorescence detector, spectrophotometer, or photometer.

* * * * *